(12) United States Patent
Eschbach

(10) Patent No.: US 11,896,439 B2
(45) Date of Patent: *Feb. 13, 2024

(54) LOAD SENSING DEVICES FOR USE IN SURGICAL INSTRUMENTS

(71) Applicant: Covidien LP, Mansfield, MA (US)

(72) Inventor: Matthew Eschbach, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 136 days.

This patent is subject to a terminal disclaimer.

(21) Appl. No.: 17/549,079

(22) Filed: Dec. 13, 2021

(65) Prior Publication Data

US 2022/0096194 A1  Mar. 31, 2022

Related U.S. Application Data

(63) Continuation of application No. 16/566,944, filed on Sep. 11, 2019, now Pat. No. 11,197,734.

(Continued)

(51) Int. Cl.
*A61B 17/072* (2006.01)
*A61B 90/00* (2016.01)
*A61B 17/00* (2006.01)

(52) U.S. Cl.
CPC ........ *A61B 90/06* (2016.02); *A61B 17/07207* (2013.01); *A61B 2017/0046* (2013.01);
(Continued)

(58) Field of Classification Search
CPC ................ A61B 17/068; A61B 17/105; A61B 17/07207; A61B 2017/0023; A61B 90/06; A61B 2017/00066; A61B 2017/00123; A61B 2017/07271; A61B 2090/065; A61B 2017/00119; A61B 2017/00734; A61B 2090/0807; A61B 2017/00725; A61B 2017/07285; A61B 2017/00929; A61B 2017/2927; A61B 2017/00415;
(Continued)

(56) References Cited

U.S. PATENT DOCUMENTS

| | | |
|---|---|---|
| 37,165 A | 12/1862 | Gary |
| 3,209,754 A | 10/1965 | Brown |

(Continued)

FOREIGN PATENT DOCUMENTS

| | | |
|---|---|---|
| CN | 101317779 A | 12/2008 |
| CN | 101683284 A | 3/2010 |

(Continued)

OTHER PUBLICATIONS

Detemple, P., "Microtechnology in Modern Health Care", Med Device Technol. 9(9):18-25 (1998).

(Continued)

*Primary Examiner* — Nathaniel C Chukwurah
(74) *Attorney, Agent, or Firm* — Carter, DeLuca & Farrell LLP

(57) ABSTRACT

A surgical end effector includes an anvil assembly; a cartridge assembly including a plurality of fasteners; a drive assembly movable longitudinally to approximate the anvil assembly relative to the cartridge assembly; and a strain gauge circuit disposed within the cartridge assembly, the strain gauge circuit configured to measure a strain imparted on the cartridge assembly by the drive assembly.

19 Claims, 12 Drawing Sheets

Related U.S. Application Data

(60) Provisional application No. 62/752,516, filed on Oct. 30, 2018.

(52) U.S. Cl.
CPC ............... *A61B 2017/07257* (2013.01); *A61B 2017/07271* (2013.01); *A61B 2090/064* (2016.02); *A61B 2562/0261* (2013.01); *A61B 2562/164* (2013.01)

(58) Field of Classification Search
CPC .......... A61B 2017/00026; A61B 2017/00017; A61B 2017/00398; A61B 90/98; A61B 2017/07264; A61B 2017/0046; A61B 2017/00473; A61B 2017/00057; A61B 2017/07278; A61B 2090/309; A61B 2017/07257
See application file for complete search history.

(56) References Cited

U.S. PATENT DOCUMENTS

| | | |
|---|---|---|
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |

(56) References Cited

U.S. PATENT DOCUMENTS

| | | |
|---|---|---|
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A * | 4/1998 | Yates ............... A61B 17/07207 606/50 |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |

(56) References Cited

U.S. PATENT DOCUMENTS

| | | |
|---|---|---|
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Ai-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 9,220,502 B2 * | 12/2015 | Zemlok ............ A61B 17/07207 |
| 10,456,137 B2 * | 10/2019 | Vendely .............. A61B 17/068 |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |

(56) References Cited

U.S. PATENT DOCUMENTS

| | | |
|---|---|---|
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0012556 A1 | 1/2009 | Boudreaux et al. |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1 | 9/2012 | Viola et al. |
| 2012/0228358 A1* | 9/2012 | Zemlok ............ A61B 17/07207 227/176.1 |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2016/0256184 A1 | 9/2016 | Shelton, IV et al. |
| 2016/0310134 A1 | 10/2016 | Contini et al. |

FOREIGN PATENT DOCUMENTS

| | | |
|---|---|---|
| CN | 102648864 A | 8/2012 |
| CN | 103654897 A | 3/2014 |
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1728475 A2 | 12/2006 |
| EP | 1813203 A2 | 8/2007 |
| EP | 3369385 A2 | 9/2018 |
| EP | 3586767 A2 | 1/2020 |
| FR | 2 849 589 A1 | 7/2004 |
| WO | 9414129 A1 | 6/1994 |
| WO | 20199414129 | 6/1994 |
| WO | 9729694 A1 | 8/1997 |
| WO | 20199729694 | 8/1997 |
| WO | 9740760 A1 | 11/1997 |
| WO | 20199740760 | 11/1997 |
| WO | 9837825 A1 | 9/1998 |
| WO | 20199837825 | 9/1998 |
| WO | 1999/52489 A1 | 10/1999 |
| WO | 0234140 A2 | 5/2002 |
| WO | 03026511 A1 | 4/2003 |
| WO | 03030743 A2 | 4/2003 |
| WO | 2004032760 A2 | 4/2004 |
| WO | 2007030753 A2 | 3/2007 |
| WO | 2007/114868 A2 | 10/2007 |
| WO | 2007118179 A2 | 10/2007 |
| WO | 2007014355 A3 | 4/2009 |
| WO | 2009143092 A1 | 11/2009 |

OTHER PUBLICATIONS

Abridged Data Sheet, "DeepCover Secure Authenticator with 1-Wire SHA-256 and 512-Bit User EEPROM", Maxim Integrated Products, Inc. pp 1-4; 42; Dec. 2012.

Data Sheet "DS28E15-1-Sire SHA-256 Secure Authenticator with 512-Bit User EEPROM"; IC-ON-LINE, Electronic Component Manufacturers, pp. 1-2; Aug. 2013.

Extended European Search Report dated Jan. 3, 2020 issued in corresponding EP Appln. 19205878.2.

European Examination Report dated Dec. 4, 2020 issued in corresponding EP Appln. No. 19205878.2.

Office Action issued in corresponding Chinese Application No. 2019110006810 dated May 31, 2023, together with English language translation (11 pages).

* cited by examiner

LOAD SENSING DEVICES FOR USE IN SURGICAL INSTRUMENTS

CROSS-REFERENCE TO RELATED APPLICATIONS

The present application is a continuation application of U.S. patent application Ser. No. 16/566,944 filed Sep. 11, 2019, now U.S. Pat. No. 11,197,734, which claims the benefit of and priority to U.S. Provisional Application No. 62/752,516, filed Oct. 30, 2018. The entire contents of which are incorporated herein by reference.

BACKGROUND

1. Technical Field

The present disclosure relates to load sensing devices for use with surgical devices. More specifically, the present disclosure relates to load sensing devices used with electromechanical surgical systems for performing surgical procedures having reusable and single use components, such as end effectors and adapters.

2. Background of Related Art

Surgical fastener apparatuses for applying fasteners or staples to tissue are well known. These fastener apparatuses include single use instruments which are preloaded with one or more staples and are disposable after a single use. Multiple use instruments are also available and are preloaded with a plurality of staples. Multiple use instruments may include a handle assembly that is electromechanically, e.g., powered, or manually actuated and a surgical loading unit. The loading unit may be a single use loading unit (SULU) or a multiple use loading unit (MULU). The loading unit includes a body and an end effector, and is attached to the handle assembly, either directly or via an adapter assembly couplable to the handle assembly. The end effector may include a cartridge which houses a plurality of staples. After use, the loading unit can be removed from the adapter assembly and replaced with a new loading unit to perform additional stapling and/or cutting operations. A drive assembly is supported within the loading unit and is engageable with an associated drive mechanism of the adapter assembly to actuate the loading unit. Due to dense packing of the mechanical components of the drive assembly there is less space for inclusion of sensors. Accordingly there is a need for load sensing devices that can be placed within the loading unit to monitor operation of the drive assembly and other components of the loading unit.

SUMMARY

Powered surgical instruments may include various sensors for providing feedback during their operation. The present disclosure provides load sensing devices disposed on a flexible circuit substrate allowing for placement of the load sensing devices in constricting spaces such as loading units and other components of surgical instruments.

Load sensing devices according to the present disclosure include strain gauges having a conductive trace formed from a resistive metal alloy, such as constantan, disposed on a dielectric substrate, such as polyamide. The strain gauges are bonded or otherwise secured to a surface of a component, including but not limited to, within one or both jaw members of a loading unit. As the component on which the strain gauge is mounted expands or compresses, (i.e., strain is applied), so do the conductive traces on the strain gauge thereby changing the overall electrical resistance of the strain gauge. The change in electrical resistance affects a measurement signal supplied to the strain gauge. In embodiments, the strain gauge may be arranged in a Wheatstone bridge circuit configuration. The change in the amplitude of the circuit is then measured to determine the amount of strain.

The typical application of a strain gauge is such that it is placed on a specific point of interest to measure the strain. This can be used for empirical testing, looking for the actual strain due to a specific loading condition, or design of a force transducer, where multiple strain gauges are placed and arranged on a part to output a calibrated signal to measure a force. The working principle of a strain gauge is based on electric resistivity, defined by Pouillett's law of formula (I): $R=\rho(l/A)$, where R is the electrical resistance, $\rho$ is material resistivity, l is the length of material, and A is cross sectional area of the material. Strain gauges include a single trace of high resistance metal arranged in such a way that the long runs of trace are in the direction of deformation interest. Thus, the strain gauge is a variable resistor changing resistance when the surface the strain gauge is bonded to changes its length due to strain. When the material that the strain gauge is bonded to deforms the l, length, variable of Pouillett's law changes causing a change in resistance, which may be measured using a Wheatstone bridge circuit.

Strain gauges may be calibrated to change a proportional amount of resistance based on the deformation of the surface the strain gauge is bonded to. This property is known as a gauge factor and is defined by the following formula (II): $GF=(\Delta R/R)/\epsilon$, where GF is the gauge factor, R is the nominal resistance, $\Delta R$ is the change in resistance, and $\epsilon$ is the strain. Gauge factor is constant in the ranges defined by the strain gauge manufacturer. For typical applications a constant gauge factor is usually used for measuring strain. However, there are instances where having a varying gauge factor throughout a strain gauge could be useful. In the present disclosure, the strain gauge is placed along a channel of a jaw member of a surgical stapler to measure the bend of the channel due to tissue compression. As a drive assembly, which also ejects staples, moves across the channel to perform the firing, the strain gauge area proximal of the I-beam is no longer bending and is effectively inactive. As a result, if the I-beam is halfway through the firing only half of the signal is being generated due to the bending. In an effort to maintain the amplitude of that signal constant throughout firing, a strain gauge with a varying gauge factor is desirable. By making the distal part of the strain gauge more sensitive, or having a higher gauge factor, the signal amplitude can be kept higher.

Conventional strain gauges may have a constant gauge factor, or a constant change in resistance for a given strain. Thus, by changing the overall shape of the conductive traces on the strain gauge a different signal response can be generated. The present disclosure provides for strain gauges that span the length of the jaw members, such that when the I-beam of the loading unit travels longitudinally through the jaw members to clamp, staple, and cut tissue there is an active region of the strain gauge disposed distally of the actuation sled. As noted above, the problem is that as the actuation sled is moved longitudinally, the active portion of the strain gauge decreases, causing an averaging effect of the entire strain gauge, which lowers the resistance change and consequently, the overall electrical signal. Currently, conventional strain gauges have a constant gauge factor throughout. The present disclosure provides for strain gauges of various shapes and dimensions and in particular their conductive grids such that different areas of the strain gauge have different gauge factors, thereby limiting the effects of averaging.

The strain gauge according to the present disclosure may also be disposed on a flexible circuit. Conventional strain gauges require solder connections or wire bond in order to complete the circuit. This can cause potential failure points and also increases the thickness of the strain gauge which prevents its placement within the loading unit. The strain gauge according to the present disclosure may also includes signal, power, and ground leads, which are also disposed as traces on the flexible circuit. This allows for the placement of the strain gauge within the loading unit.

The strain gauge includes a resistance material having traces formed from a metal alloy, such as constantan, on a dielectric substrate, such as polyamide. In embodiments, any alloy having a negative thermal coefficient of resistance, high resistivity, and strong mechanical properties for withstanding strain may be used to form the resistance material. The traces of the resistance material are made such that they optimally change in resistance in response to the component, to which the strain gauge is attached, being deformed. The strain gauge also includes a conductive material disposed over the resistance material. The conductive material may be formed from a low resistivity metal, such as copper.

The strain gauge is formed by depositing the resistance material in a predetermined pattern in a first, e.g., proximal, portion, and an uninterrupted layer in a second, e.g. distal, portion. The predetermined pattern of the resistance material is masked and the conductive material traces are disposed directly over the uninterrupted layer of the resistance material. This configuration obviates the need for additional insulation layers, thereby minimizing the thickness of the strain gauge. Since the resistance material has a higher resistance than the conductive material, the current only flows through the conductive material that is disposed over the uninterrupted layer of the resistance material.

According to one embodiment of the present disclosure, a surgical end effector is provided. The surgical end effector includes an anvil assembly; a cartridge assembly including a plurality of fasteners; a drive assembly movable longitudinally to approximate the anvil assembly relative to the cartridge assembly; and a strain gauge circuit disposed within the cartridge assembly, the strain gauge circuit configured to measure a strain imparted on the cartridge assembly by the drive assembly.

According to another embodiment of the present disclosure, a surgical instrument is provided. The surgical instrument includes a handle assembly including a controller and a power source; an adapter assembly including a proximal end portion coupled to the handle assembly and a distal end portion; and a loading unit coupled to the distal end portion of the adapter assembly. The loading unit including a surgical end effector having: an anvil assembly; a cartridge assembly including a plurality of fasteners; and a drive assembly movable longitudinally to approximate the anvil assembly relative to the cartridge assembly. The surgical end effector also includes a strain gauge circuit disposed within the cartridge assembly and electrically coupled to the controller and the power source, the strain gauge circuit configured to measure a strain imparted on the cartridge assembly by the drive assembly and to transmit a measurement signal to the controller.

According to one aspect of any of the above embodiments, the strain gauge circuit includes a flexible circuit. The flexible circuit may include a first flexible dielectric substrate; a resistive sensor layer disposed over the first flexible dielectric substrate; a conductive layer disposed over the resistive sensor layer; and a second flexible dielectric substrate disposed over the resistive sensor layer and the conductive layer.

According to another aspect, the resistive sensor layer includes a strain gauge and a continuous layer. The conductive layer includes a first conductive trace and a second conductive trace, each of which is coupled to the strain gauge.

According to a further aspect, the strain gauge includes a continuous trace having a first end and a second end, the first end coupled to the first conductive trace and the second end coupled to the second conductive trace.

According to yet another aspect, the strain gauge includes a variable gauge factor. The strain gauge may include a variable cross-section. The strain gauge may further include a pair of parallel grid lines, each of which has a tapered shape thereby providing the variable cross-section. The strain gauge may further include a plurality of grid lines of varying length providing the variable cross-section.

According to one aspect strain gauge circuit includes a strain gauge portion and a lead portion, the lead portion includes a slack portion having at least one turn.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
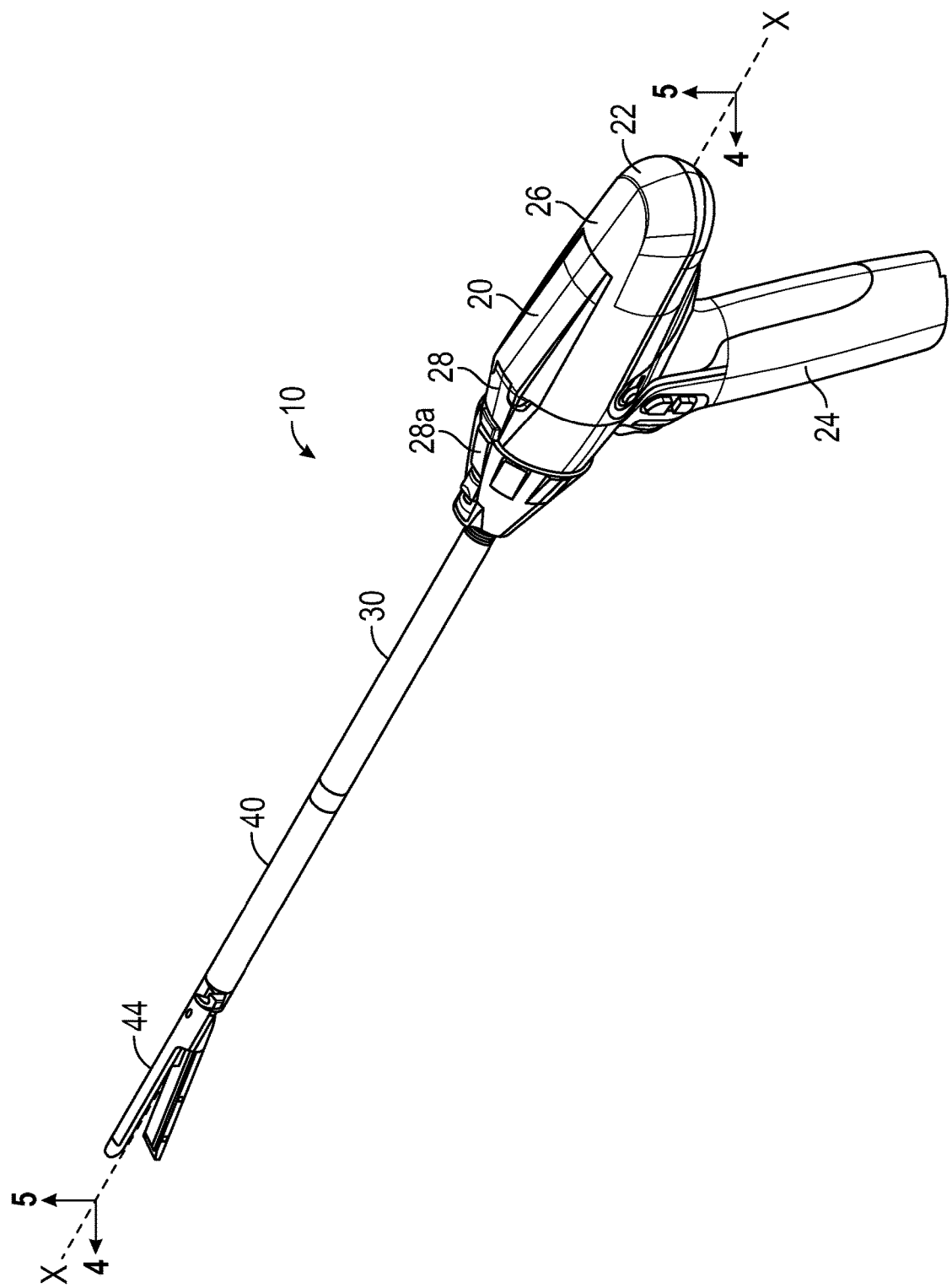
FIG. 1 is a perspective view of a handheld surgical instrument, an adapter assembly, an end effector having a reload and an anvil assembly according to an embodiment of the present disclosure.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the instrument or component thereof that is closer to the clinician and the term "distal" will refer to the portion of the instrument or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

The present disclosure relates to flexible strain gauge circuits that may be used with surgical instruments. In particular, the size of the flexible strain gauge circuits according to the present disclosure allows for placement of these circuits within tight confines of loading units and their end effectors. The flexible strain gauge circuits also include strain gauges that have a variable gauge factor to compensate for variable strain that is imparted on the end effectors during use. The variable strain is caused by longitudinal translation of a drive assembly that actuates that end effectors. The variable gauge factor of the strain gauges is achieved by providing for a variable cross-sectional area of the strain gauge.

With reference to FIG. 1, a powered surgical instrument 10 includes a handle assembly 20, which is configured for selective connection with an adapter assembly 30, which in turn, is configured for selective connection with an end effector, such a loading unit 40. Although generally referred to as being a powered surgical instrument, it is contemplated that the surgical instrument 10 may be a manually actuated and may include various configurations.

Figure 2:
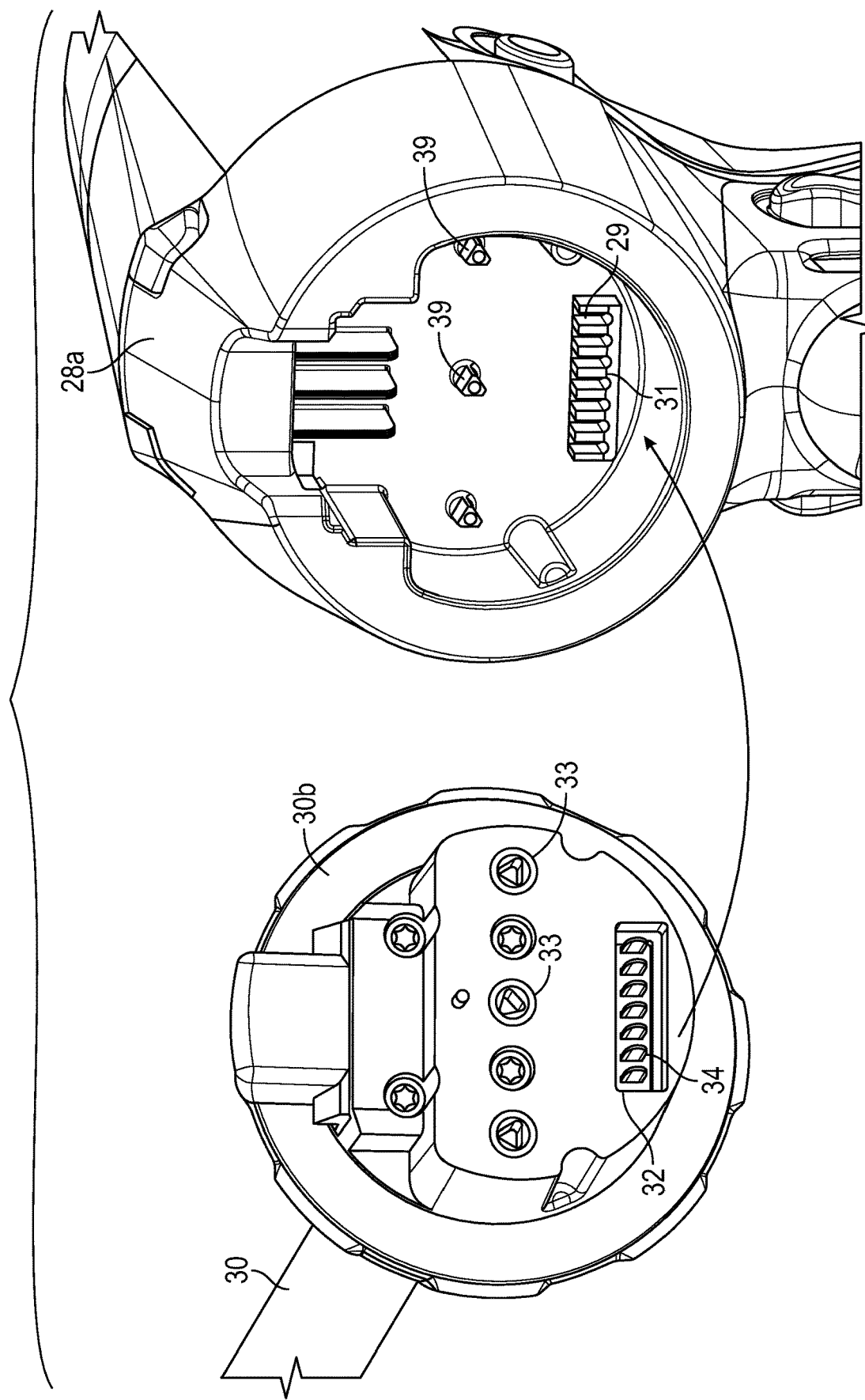
FIG. 2 is a perspective view illustrating a connection of the adapter assembly and the handle assembly of FIG. 1 according to an embodiment of the present disclosure.

The handle assembly 20 includes a handle housing 22 having a lower housing portion 24, an intermediate housing portion 26 extending from and/or supported on a portion of the lower housing portion 24, and an upper housing portion 28 extending from and/or supported on a portion of the intermediate housing portion 26. As shown in FIG. 2, a distal portion of the upper housing portion 28 defines a nose or connecting portion 28a that is configured to accept a proximal end portion 30b of the adapter assembly 30.

Figure 3:
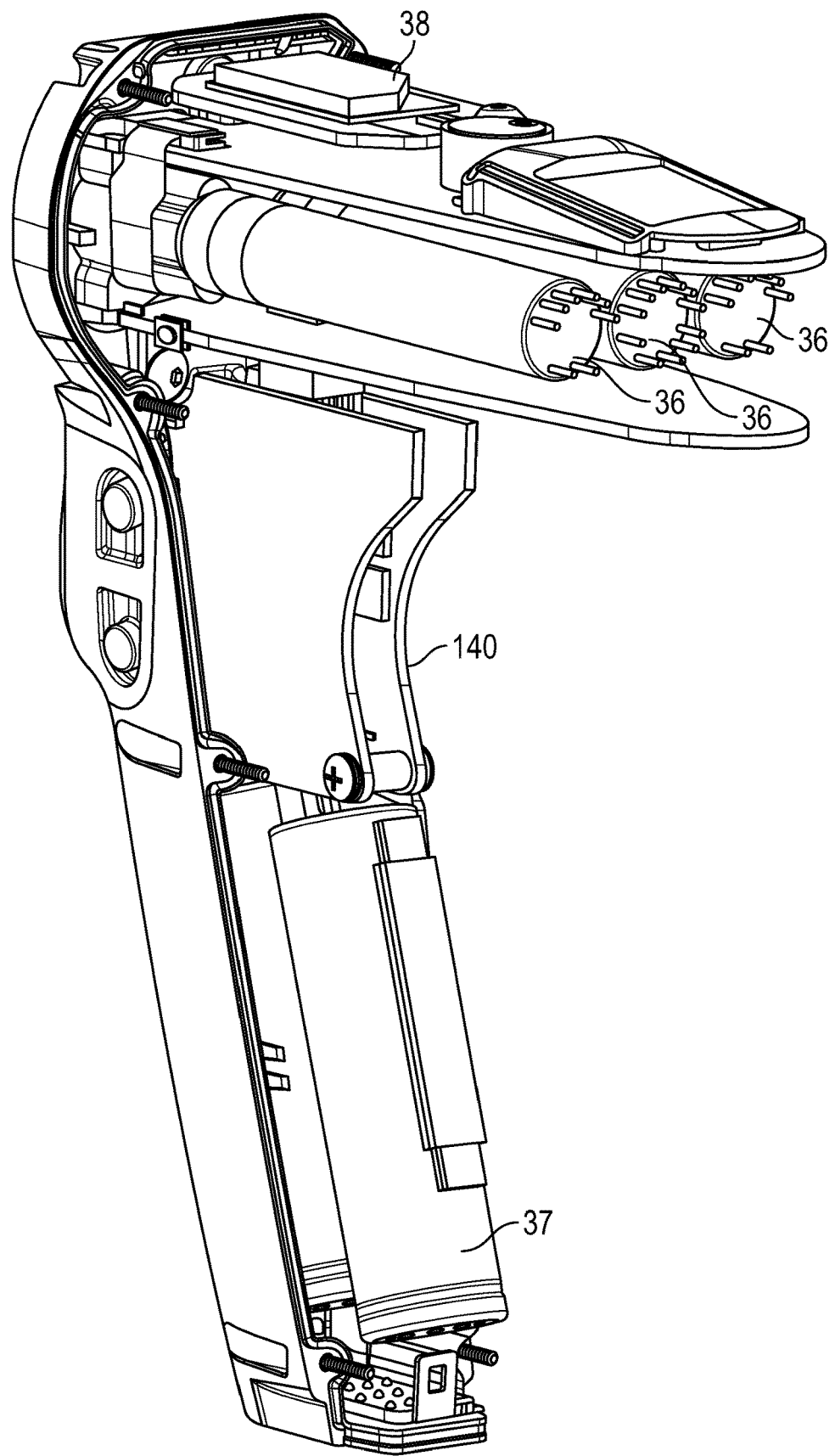
FIG. 3 is perspective view of internal components of the handle assembly according to an embodiment of the present disclosure.

With reference to FIG. 2, the connecting portion 28a includes an electrical receptacle 29 having a plurality of electrical contacts 31, which are in electrical communication with electronic (e.g., main controller 38) and electrical components (e.g., power source 37) of the handle assembly 20 (FIG. 3). The adapter assembly 30 includes a counterpart electrical connector 32 that is configured to engage the electrical receptacle 29. The electrical connector 32 also includes a plurality of electrical contacts 34 that engage and electrically connect to their counterpart electrical contacts 31.

With reference to FIG. 3, the handle assembly 20 includes one or more motors 36 which are coupled to a power source 37. The handle assembly 20 also includes a main controller 38 for operating the motors 36 and other electronic components of the handle assembly 20, the adapter assembly 30, and the loading unit 40. The motors 36 are coupled to corresponding drive shafts 39 (FIG. 2), which are configured to engage sockets 33 on the proximal end portion 30b, such that rotation of the drive shafts 39 is imparted on the sockets 33.

Figure 4:
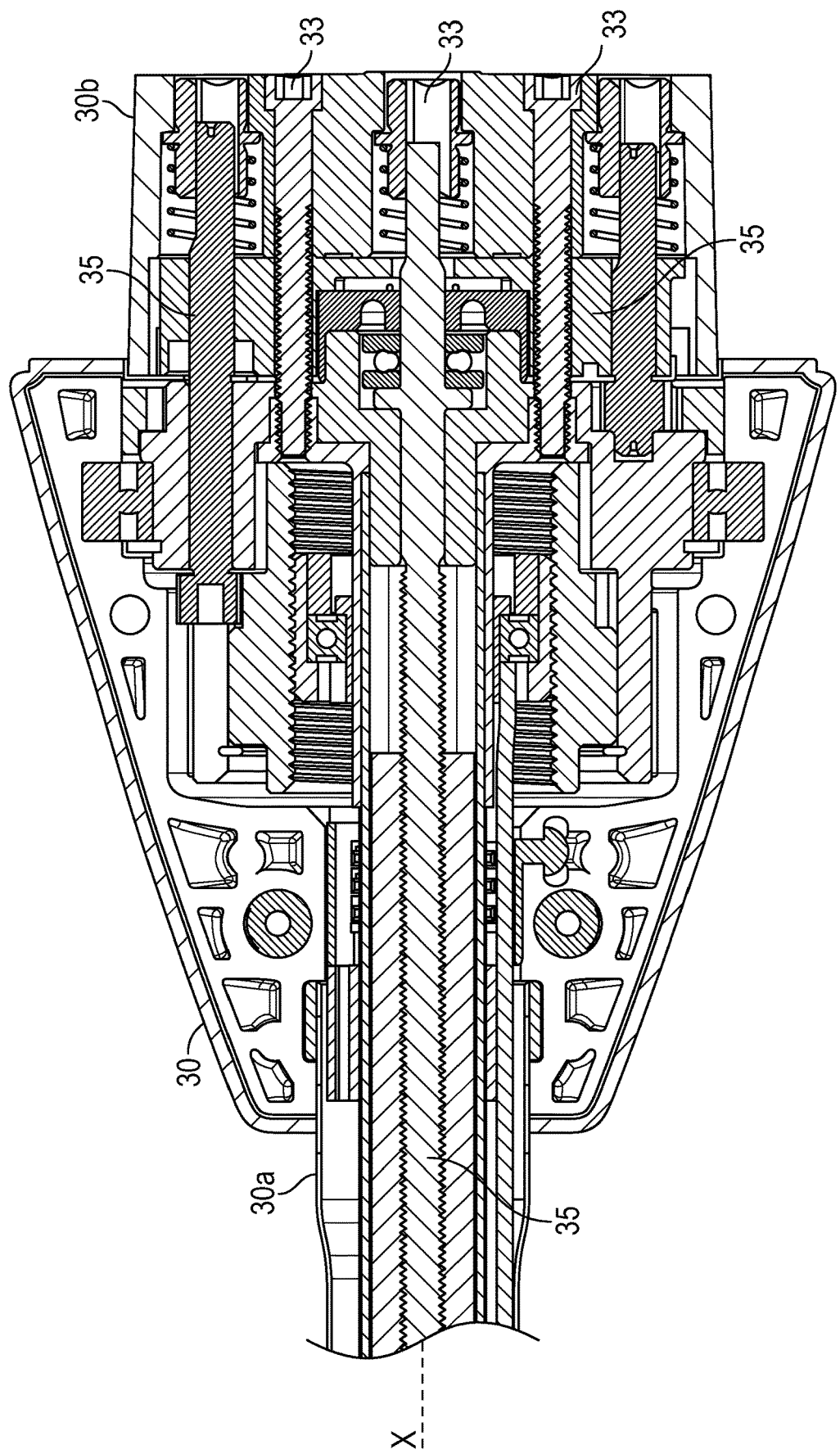
FIG. 4 is cross-sectional view of the adapter assembly of FIG. 1 taken along a section plane "4-4" according to an embodiment of the present disclosure.
Figure 5:
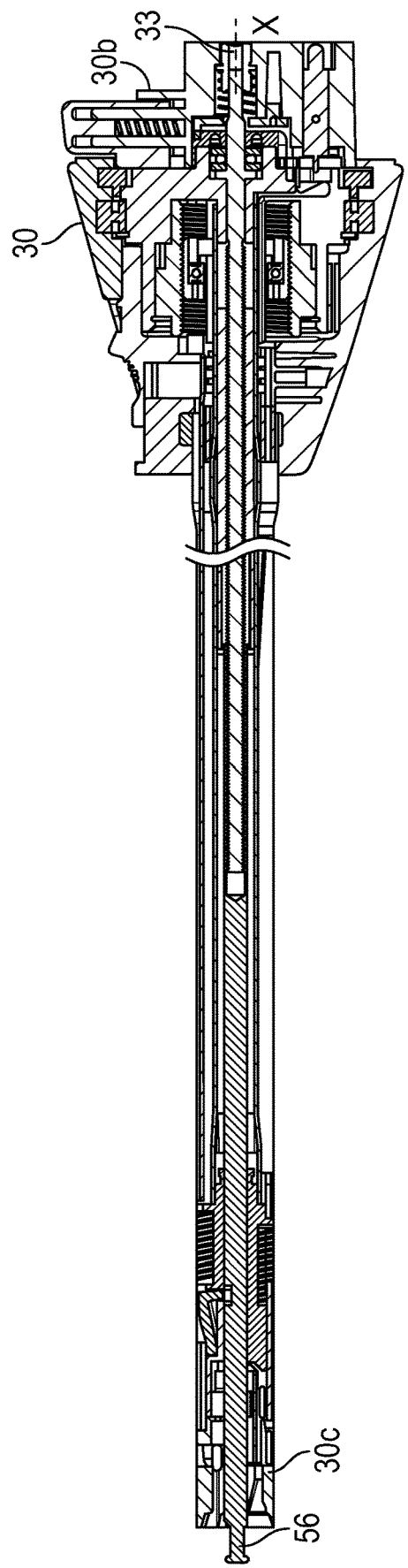
FIG. 5 is cross-sectional view of the adapter assembly of FIG. 1 taken along a section plane "5-5" according to an embodiment of the present disclosure.

With reference to FIGS. 4 and 5, the adapter assembly 30 includes a tubular housing 30a that extends between a proximal end portion 30b that is configured for operable connection to the connecting portion 28a of the handle assembly 20 and an opposite, distal end portion 30c that is configured for operable connection to the loading unit 40. The adapter assembly 30 includes actuation assemblies 35 each of which is coupled to one of the sockets 33. The actuation assemblies 35 are configured to transfer rotational motion of the sockets 33 into linear motion and/or rotational motion, such that the adapter assembly 30 is configured to convert a rotational motion provided by the handle assembly 20 into axial translation for rotating the adapter assembly 30 about a longitudinal axis X-X, articulate the loading unit 40, clamp tissue, eject fasteners, and cut fastened tissue.

Figure 6:
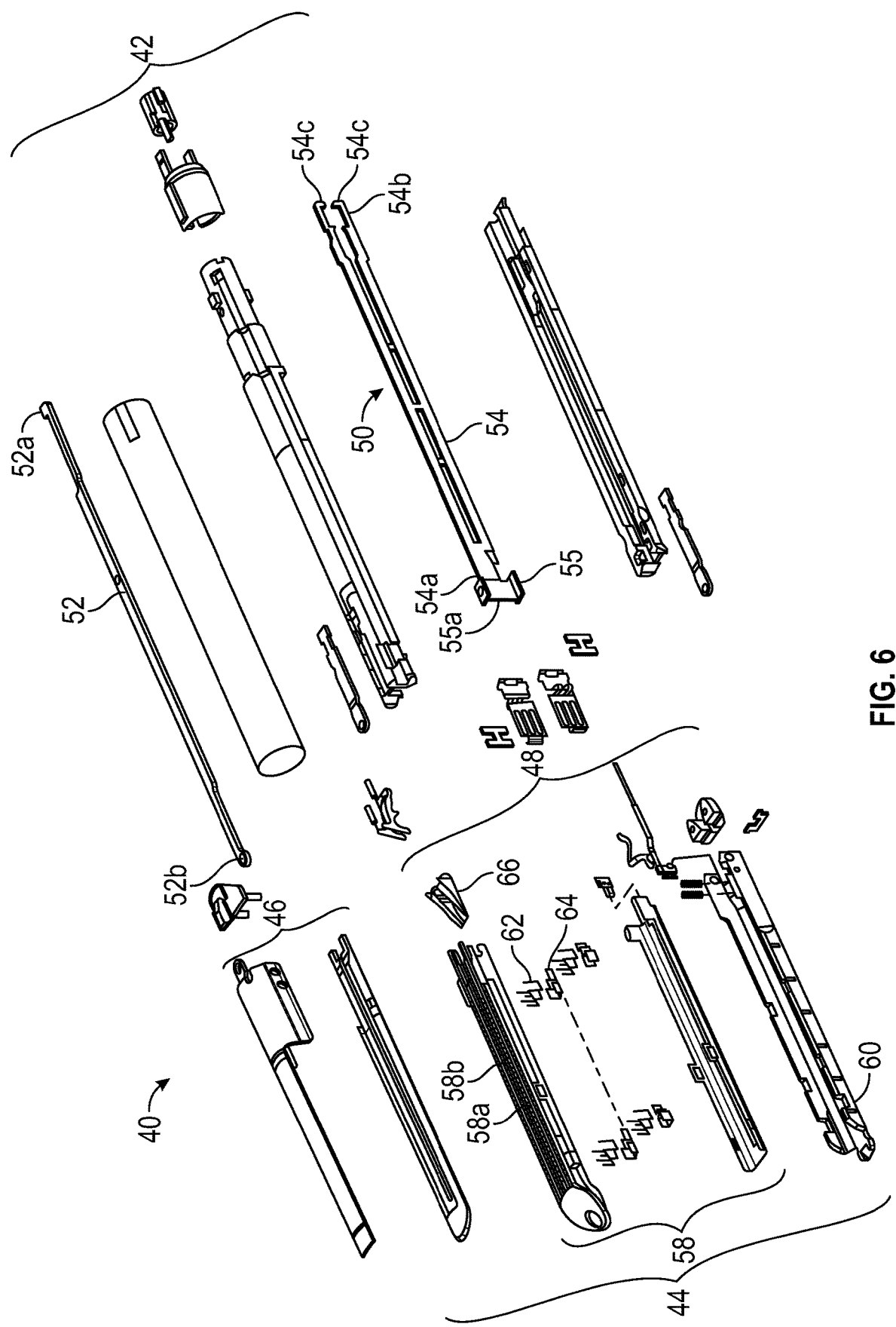
FIG. 6 is a perspective view, with parts separated, of the surgical loading unit of FIG. 1.

With reference to FIGS. 1 and 6, an embodiment of the loading unit 40 is shown. The loading unit 40 includes a proximal body portion 42 and a surgical end effector 44. Proximal body portion 42 is releasably attached to the distal end portion 30c of adapter assembly 30, and end effector 44 is pivotally attached to a distal end of proximal body portion 42. End effector 44 includes an anvil assembly 46 and a cartridge assembly 48. Cartridge assembly 48 is pivotal in relation to anvil assembly 46 and is movable between an open or unclamped position and a closed or clamped position. Proximal body portion 42 includes a drive assembly 50 and an articulation link 52.

Drive assembly 50 includes a flexible drive beam 54 having a distal end portion 54a and a proximal engagement section 54b. The distal end portion 54a includes an I-beam 55 having a knife 55a. The I-beam 55 is configured to travel through the anvil assembly 46 and the cartridge assembly 48, thereby pushing the anvil assembly 46 toward the cartridge assembly 48 to clamp tissue. The proximal engagement section 54b includes diametrically opposed inwardly extending fingers 54c that engage a drive member 56 (FIG. 5) to fixedly secure drive member 56 to the proximal end of drive beam 54. Drive member 56 is actuated by one of the actuation assemblies 35 of adapter assembly 30.

Cartridge assembly 48 of end effector 44 includes a staple cartridge 58 removably supported in a carrier 60. Staple cartridge 58 defines a central longitudinal slot 58a, and a plurality of linear rows of staple retention slots 58b positioned on each side of the central longitudinal slot 58a. Each of the staple retention slots 58b receives a single staple 62 and a portion of a staple pusher 64. During operation of the surgical instrument 10, drive assembly 50 abuts an actuation sled 66 and pushes actuation sled 66 through the staple cartridge 58. As the actuation sled 66 moves through staple cartridge 58, cam wedges of the actuation sled 66 sequentially engage staple pushers 64 to move staple pushers 64 vertically within staple retention slots 58*b* and sequentially eject a single staple 62 therefrom for formation against an anvil plate 46*a* of anvil assembly 46.

Proximal body portion 42 of surgical loading unit 40 includes an articulation link 52 having a hooked proximal end portion 52*a* which extends from a proximal end of surgical loading unit 40 which engages an opposing articulation link (not shown) coupled to another one of the actuation assemblies 35 of the adapter assembly 30. Articulation link 52 has a distal end portion 52*b* pivotably secured to end effector 44.

Figure 7:
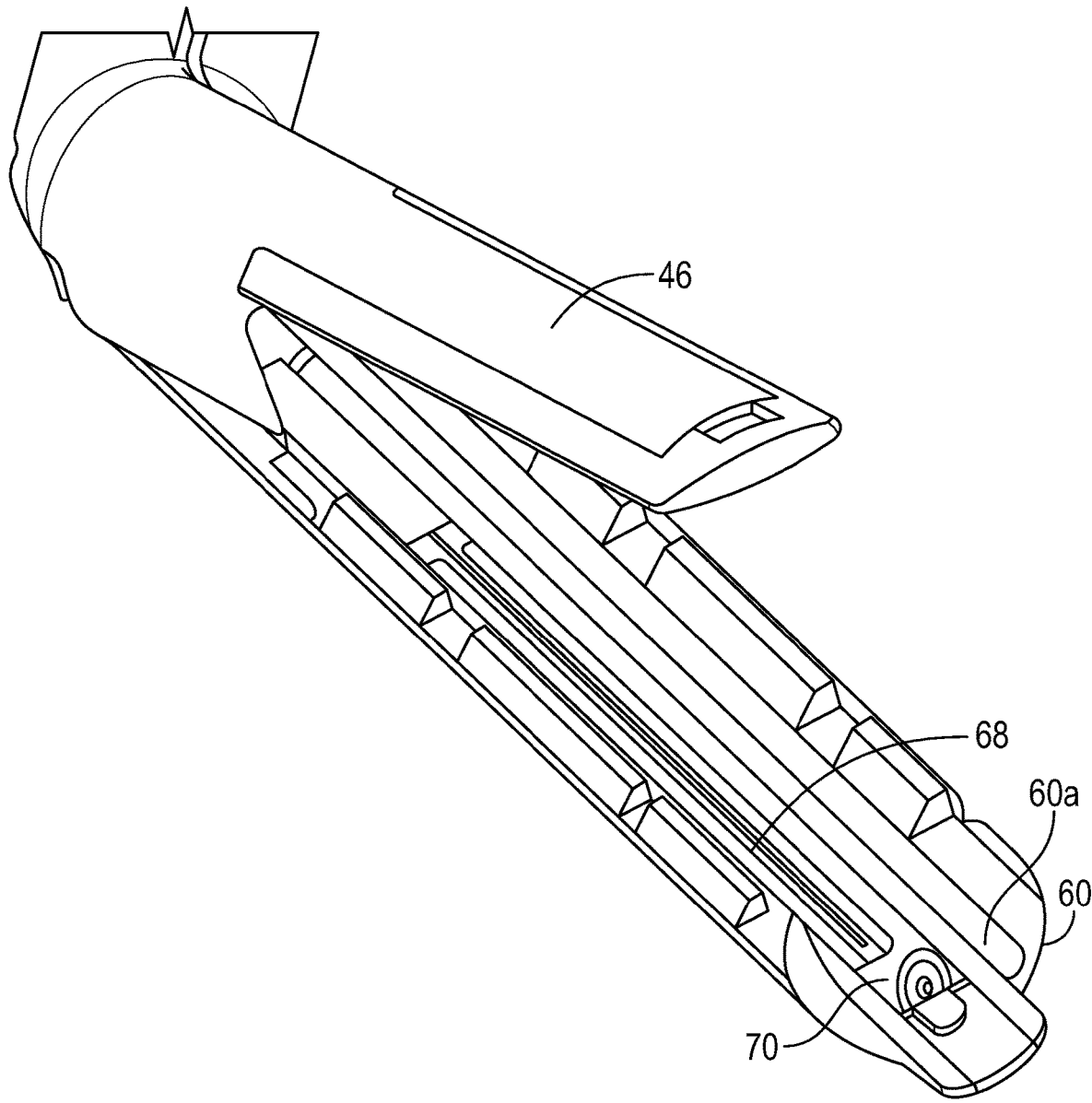
FIG. 7 is a perspective view of an end effector of the surgical loading unit of FIG. 1 with a strain gauge circuit according to an embodiment of the present disclosure.
Figure 8:
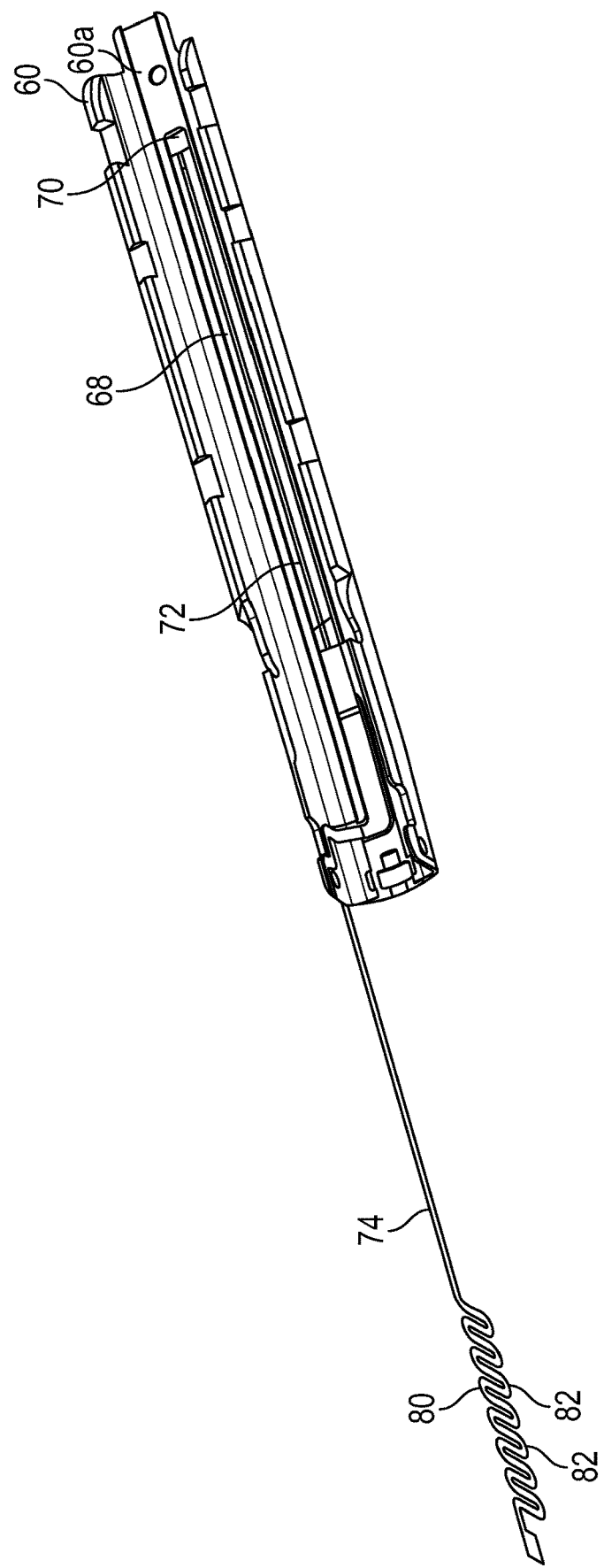
FIG. 8 is a perspective view of a strain gauge circuit disposed within a carrier of the end effector of FIG. 7 according to an embodiment of the present disclosure.
Figure 9:
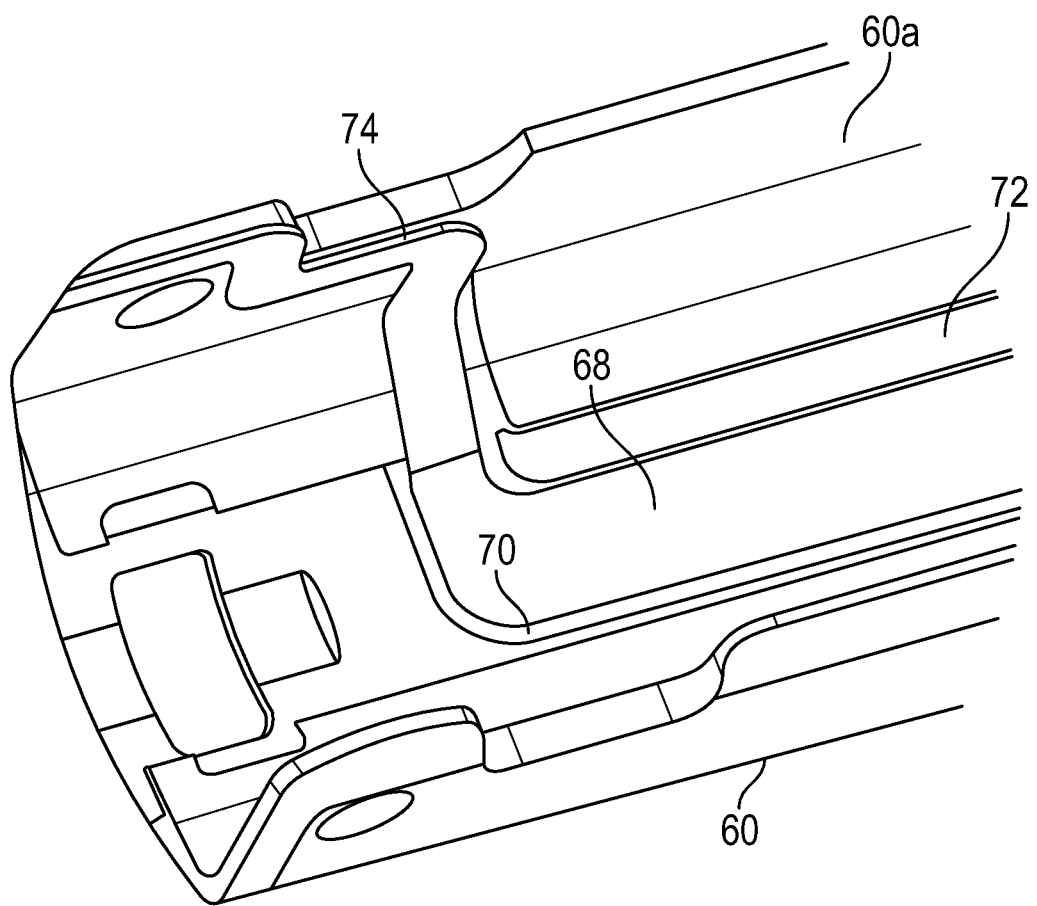
FIG. 9 is an enlarged perspective view of a proximal portion of the carrier of FIG. 8 according to an embodiment of the present disclosure.

With reference to FIGS. 7-9, the end effector 44 includes a strain gauge circuit 68 disposed within the cartridge assembly 48. In embodiments, a second strain gauge circuit may be disposed within the anvil assembly 46. The carrier 60 includes a depression 70 defined on an inner bottom surface 60*a* and an inner side surface of the carrier 60. The depression 70 is configured to accommodate the strain gauge circuit 68 while allowing the staple cartridge 58 to fit over the strain gauge circuit 68. The strain gauge circuit 68 may be secured within the depression 70 by bonding.

Figure 10:
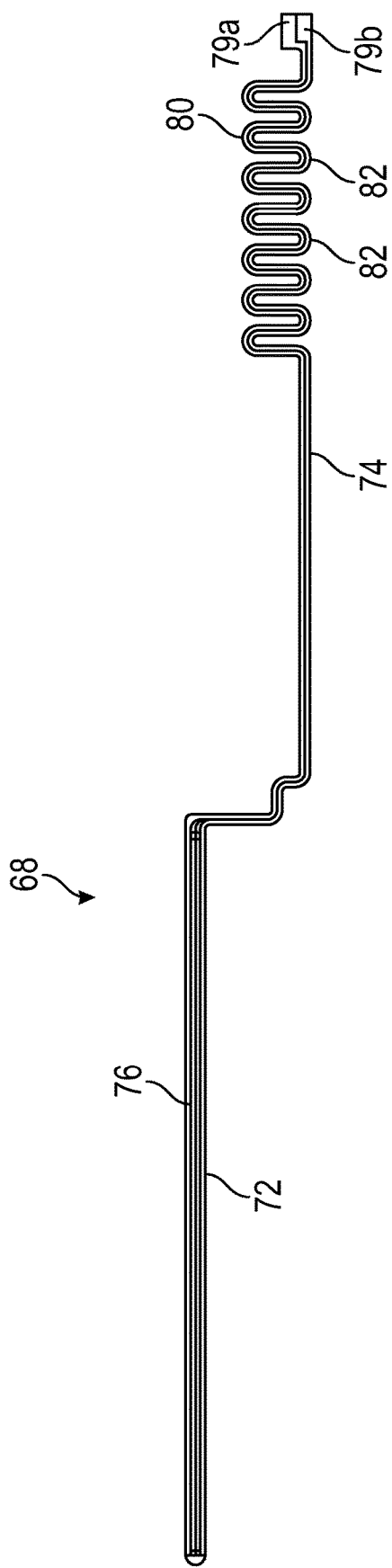
FIG. 10 is a top view of a resistive sensor layer disposed on a first flexible dielectric substrate of the strain gauge circuit of FIG. 7 according to an embodiment of the present disclosure.
Figure 11:
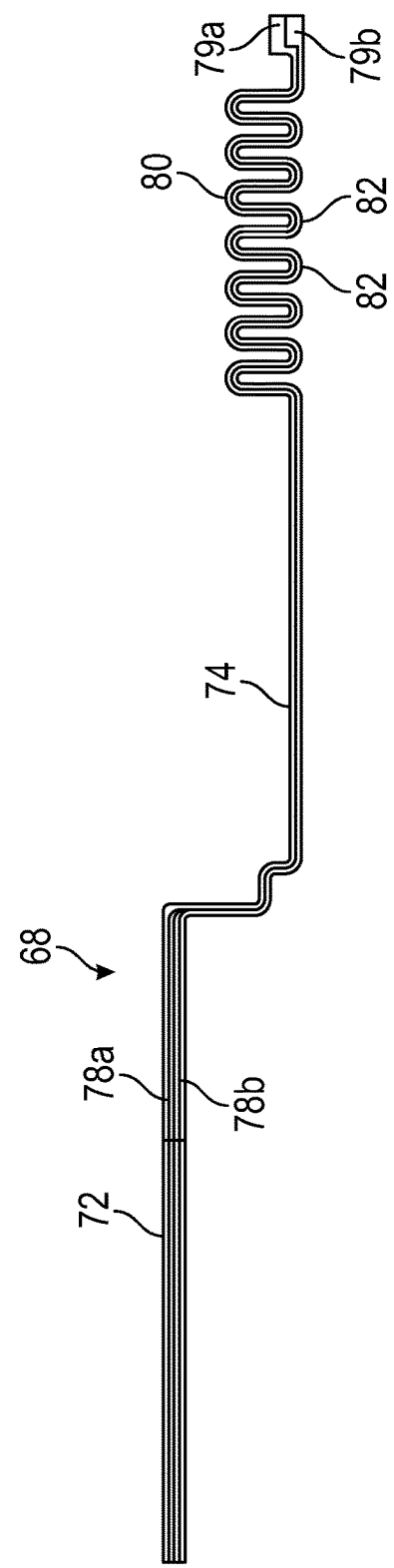
FIG. 11 is top view of a conductive layer disposed on a second flexible dielectric substrate of the strain gauge circuit of FIG. 7 according to an embodiment of the present disclosure.
Figure 12:
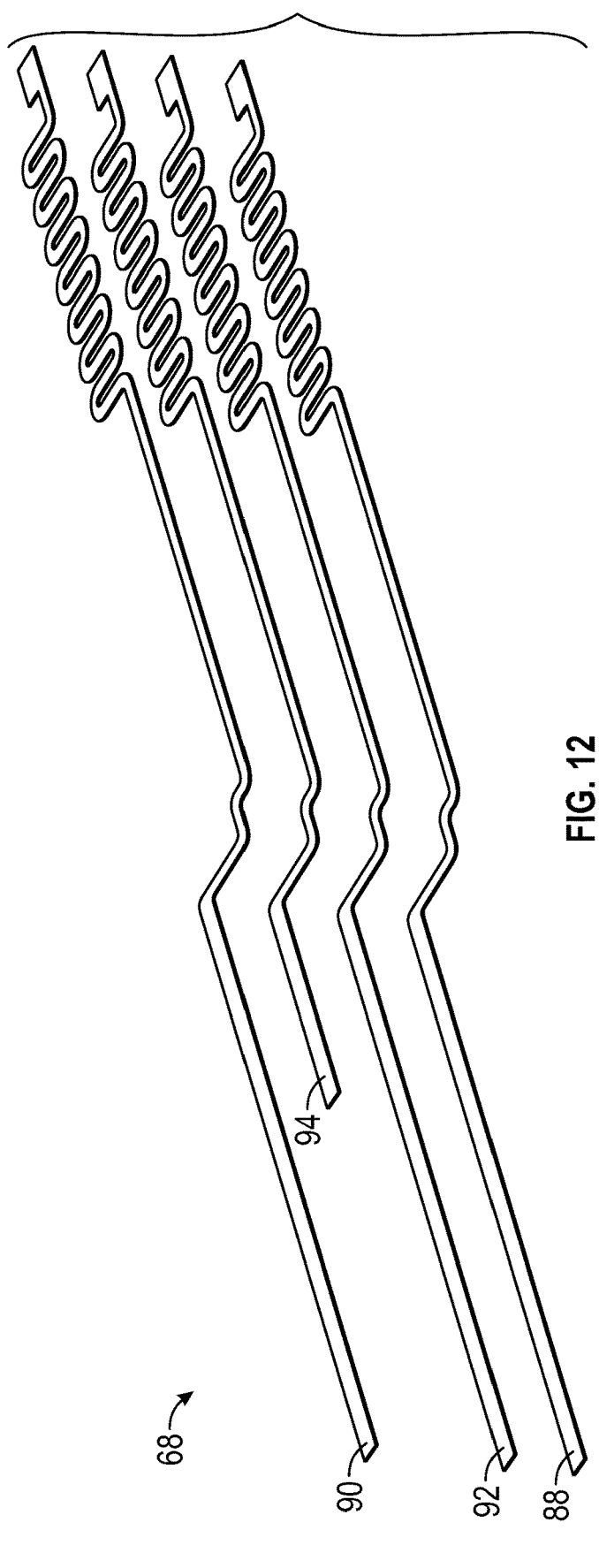
FIG. 12 is a perspective view, with layers separated, of the strain gauge circuit of FIG. 7 according to an embodiment of the present disclosure.

With reference to FIGS. 10 and 11, the strain gauge circuit 68 includes a strain gauge portion 72 and a lead portion 74. The strain gauge portion 72 includes a strain gauge 76 and the lead portion 74 includes first and second conductive traces 78*a* and 78*b* coupling the strain gauge 76 to the main controller 38 and the power source 37. The lead portion 74 may include any number of segments to allow for routing the strain gauge circuit 68 within the loading unit 40 as shown in FIG. 9. The lead portion 74 also includes a slack portion 80 having one or more turns 82, which allow the slack portion 80 additional freedom of movement within the loading unit 40. Each of traces 78*a* and 78*b* is coupled to contact pads 79*a* and 79*b*, respectively, which are disposed at a proximal end portion of the lead portion 74. The contact pads 79*a* and 79*b* are configured to couple to electrical contacts (not shown) of the adapter assembly 30, which in turn, coupled the strain gauge circuit 68 to the power source 37 and the main controller 38 of the handle assembly 20.

With reference to FIGS. 10-13, the strain gauge circuit 68 is formed as a flexible circuit 86 having a first flexible dielectric substrate 88 and a second flexible dielectric substrate 90, which enclose a resistive sensor layer 92 and a conductive layer 94. The dielectric substrates 88 and 90 may be formed from any suitable flexible dielectric material including, but not limited to, polyester, polyimide, polyethylene naphthalate, polyetherimide, fluoropolymers, polyether ether ketone, and combinations thereof. The resistive sensor layer 92 may be formed from any metal alloy having a negative thermal coefficient of resistance (to minimize and/or prevent effects of temperature variation on resistance), high resistivity (resistivity above $45.0 \times 10^{-8}$ $\Omega \cdot m$), and strong mechanical properties to withstand mechanical strain). Suitable alloys for use as the resistive sensor layer 92 include any alloy formed from copper, nickel, manganese, and combinations thereof, such as constantan and manganin. The conductive layer 94 is formed from any suitable conductive material such as metals, such as copper, silver, and the like, metal alloys, electroconductive polymers, and combinations thereof.

Figure 13:
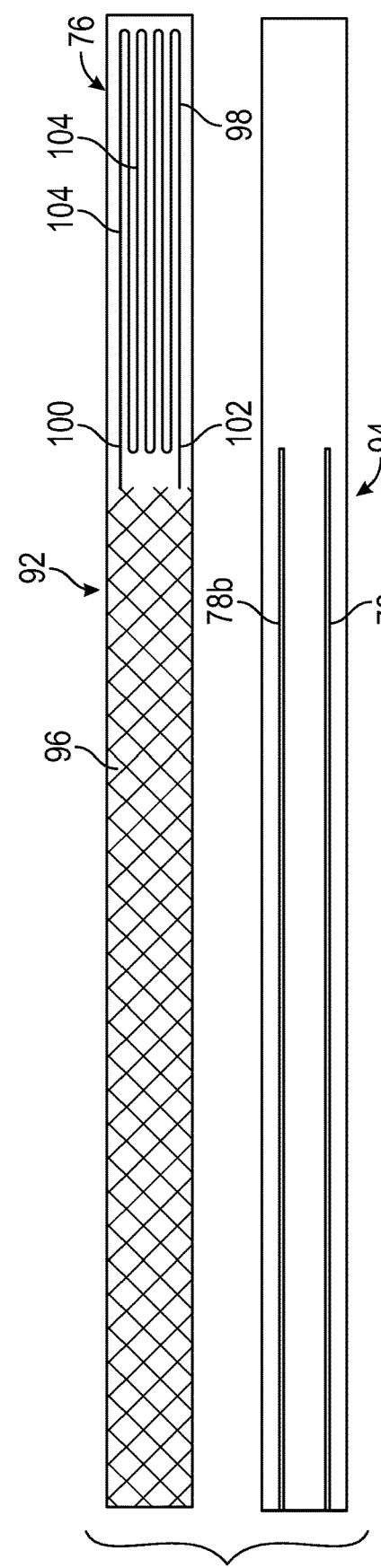
FIG. 13 is a top view of the resistive sensor layer and the conductive layer of the strain gauge circuit of FIG. 7 according to an embodiment of the present disclosure.

The resistive sensor layer 92 includes the strain gauge 76 and a continuous segment 96 that are disposed on the first dielectric substrate 88. The strain gauge 76 includes a continuous trace 98 having a first end 100 and a second end 102 the continuous trace 98 arranged in any suitable grid pattern, such as one having a plurality of parallel grid lines 104 interconnected at their opposite ends, as shown in FIG. 13. The first and second ends 100 and 102 of the continuous trace 98 are coupled to the first conductive trace 78*a* and the second conductive trace 78*b* of the conductive layer 94. The first and second conductive traces 78*a* and 78*b* overlay the continuous segment 96 of the resistive sensor layer 92. Each of the first and second conductive traces 78*a* and 78*b* are coupled to the first and second ends 100 and 102 of the continuous trace 98 providing for transmission of a measurement signal through the strain gauge 76.

Prior to forming the conductive traces 78*a* and 78*b*, the strain gauge 76 may be masked. The resistive sensor layer 92 and the conductive layer 94 may be applied to the first dielectric substrate 88 using any subtractive (e.g., etching) or additive (e.g., screen printing) technique for forming metal layers on a flexible dielectric substrate. Since the resistive sensor layer 92 has a higher resistance than the conductive traces 78*a* and 78*b* of the conductive layer 94, electrical current of the measurement signal travels only through the strain gauge 76 and the conductive traces 78*a* and 78*b*. This configuration obviates the need for an insulative layer between the resistive sensor layer 92 and the conductive layer 94 thereby making the strain gauge circuit 68 thinner and allowing for placement thereof within the depression 70 of the carrier 60.

The strain gauge circuit 68 is configured to measure the strain imparted on the end effector 44, and in particular, the cartridge assembly 48 during actuation of the drive assembly 50. As noted above, as the drive assembly 50 is moved distally, the drive assembly 50 closes the anvil assembly 46 and pushes the actuation sled 66 through the staple cartridge 58. The actuation sled 66 engages staple pushers 64, which eject staples 62, sealing tissue. Simultaneously, the knife 55*a* also cuts the sealed tissue. Accordingly, during movement of the drive assembly 50, the carrier 60 is bent due to tissue compression and other forces.

As the drive assembly 50, and in particular, the I-beam 55, moves across the channel to perform the clamping, stapling, and cutting, a proximal area of the strain gauge 76, namely, the area that is proximal of the I-beam 55, is no longer bending and is effectively inactive. Thus, if the I-beam 55 is halfway through the actuation movement only half of the signal is being generated by the strain gauge 76. The present disclosure provides for novel strain gauge designs that prevent the signal from decreasing throughout firing. In embodiments, the strain gauges according to the present disclosure have a varying gauge factor. In particular, a distal portion of the strain gauge is more sensitive, e.g., has a higher gauge factor, than a proximal portion of the strain gauge, such that an amplitude of the measurement signal is higher as the firing progresses.

The total resistance change of the strain gauge 76 is dependent on the strain imparted on the strain gauge 76. Thus, if the strain is constant, as is in axial loading, then the gauge factor could be used to calculate the known strain. However, the carrier 60 acts as a cantilever beam that is being bent by the I-beam 55 drive assembly 50. The carrier 60, and the depression 70 within which the strain gauge 76 is disposed, begins bending distally of the I-beam 55, as a result, in embodiments where the strain gauge 76 is too long (e.g., above 3 centimeters), there is no bending proximally of the I-beam 55.

The strain that is related to the changing position of the I-beam 55 may be calculated using formula (III): $\epsilon_a = \beta e^{-\alpha x}$, where $\epsilon_a$ is the axial strain, $\beta$ and $\alpha$ are constants, and x is the position of the I-beam 55 within the anvil assembly 46 and the cartridge assembly 48.

The following formula (IV) may be used to determine the change in resistance for a given strain:

$$\frac{\Delta R}{R}(x) = \epsilon_a(x) - 2\frac{dD}{D(x)}$$

where D is an element of the cross-sectional area of the strain gauge 76.

The total change in resistance can be determined as an integral of formula (IV) from the position, k, of the I-beam 55 to the end of the reload, L, using the formula (V):

$$\int_k^L \frac{\Delta R}{R}(x)dx.$$

In order for there to be a constant resistance change over all positions of the I-beam 55, the derivative of formula (V) with respect to position k should be constant as shown in formula (VI):

$$\frac{d}{dk}\int_k^L \frac{\Delta R}{R}(x)dx = 0.$$

Evaluating formula (VI) by substituting formula (IV), the following formula (VII) is derived:

$$0 = \epsilon_a(k) - 2\frac{\frac{dD}{dx}(k)}{D(k)}.$$

In focusing on the second term of formula (VII), it shows that if the change in the wire cross-section is divided by the wire cross-section is equal to the axial strain for all positions of the I-beam 55, there will be a constant resistance change. Formula (VII) assumes a constant bend characteristic and that the cross-sectional change due to the Poisson's effect is minimal. Thus, formula (VII) illustrates that changing the shape of the wire or trace on a strain gauge could produce a constant resistance change.

Figure 14:
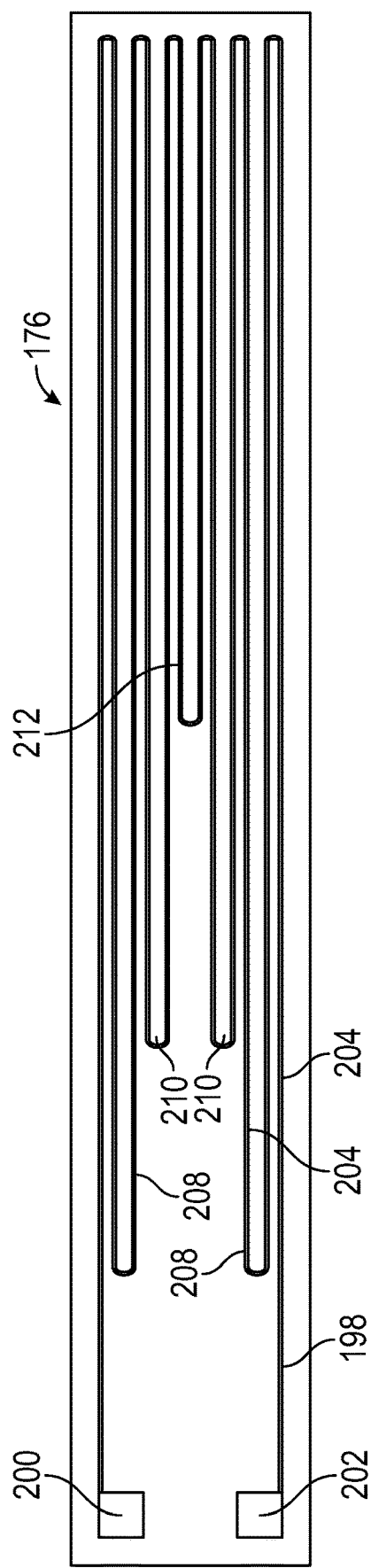
FIG. 14 is a top view of a strain gauge of the strain gauge circuit of FIG. 7 according to an embodiment of the present disclosure.

The strain gauges according to the present disclosure may also incorporate other grid patterns having a constant resistance change to provide for a variable gauge factor. With reference to FIG. 14, a strain gauge 176 is shown, which may be used in the strain gauge circuit 68. The strain gauge 176 includes a continuous trace 198 having a first end 200 and a second end 202. The continuous trace 198 includes a plurality of parallel grid lines 204 of varying length that are interconnected at their opposite ends. The length of the grid lines 204 decreases from outer to inner grid lines 204. In particular, the grid lines 204 are arranged in a plurality of pairs, two first pairs 208 being the longest aside from two outermost grid lines 204, two second pairs 210 being of intermediate length, and a middle pair 212 being the shortest. In addition, the grid lines 204 are arranged in a symmetrical pattern about a longitudinal axis defined by the strain gauge 176. It is envisioned that the strain gauge 176 may include any number of grid lines 204 arranged in any number of pairs of decreasing length (from outside in) in order to compensate for the variable strain of the I-beam 55 by varying the cross-sectional area of the strain gauge 176 in a longitudinal direction. Varying of the cross-sectional area, namely, by increasing the area in a longitudinal direction from proximal and distal direction, achieves a consistent ΔR across the entire length of the strain gauge 176.

Figure 15:
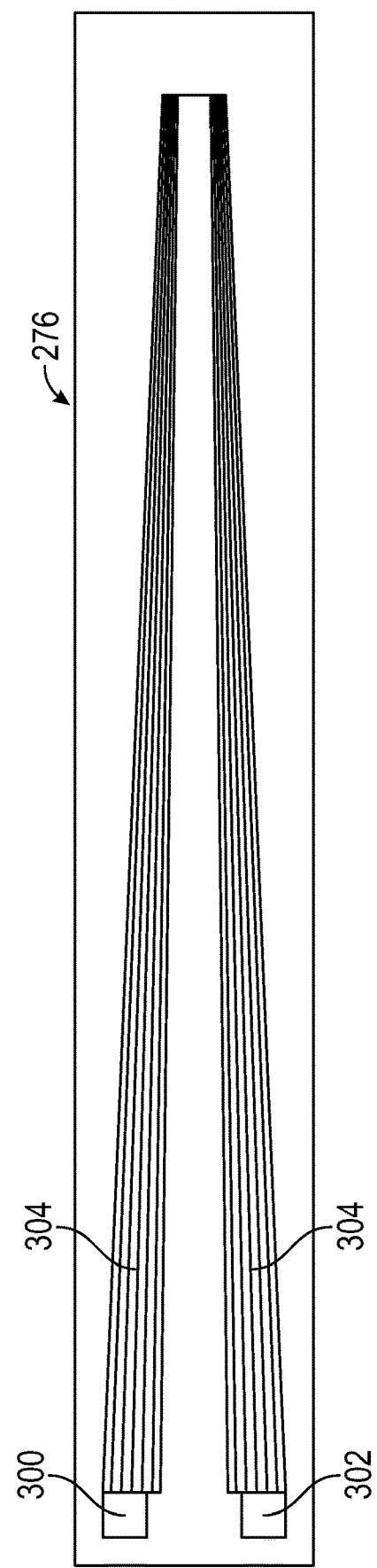
FIG. 15 is a top view of a strain gauge of the strain gauge circuit of FIG. 7 according to another embodiment of the present disclosure.

With reference to FIG. 15, a strain gauge 276 is shown, which may also be used in the strain gauge circuit 68. The strain gauge 276 includes a pair of parallel grid lines 304 interconnected at their distal ends 300 and 302. The grid lines 304 are arranged in a symmetrical pattern about a longitudinal axis defined by the strain gauge 76. Each of the grid lines 304 has a tapered shape with decreasing width from in a longitudinal direction from proximal and distal direction. This configuration also compensates for the variable strain of the I-beam 55 by varying the cross-sectional area of the strain gauge 276 in a longitudinal direction. Varying the cross-sectional area achieves a consistent ΔR across the entire length of the strain gauge 276.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A surgical end effector comprising:
   a housing
   a drive assembly movable within the housing;
   a strain gauge circuit disposed within the housing, the strain gauge circuit configured to measure a strain imparted on the housing by the drive assembly, the strain gauge circuit includes a flexible circuit, the flexible circuit having:
   a first flexible dielectric substrate;
   a resistive sensor layer disposed over the first flexible dielectric substrate;
   a conductive layer disposed over the resistive sensor layer; and
   a second flexible dielectric substrate disposed over the resistive sensor layer and the conductive layer.

2. The surgical end effector according to claim 1, wherein the resistive sensor layer includes a strain gauge and a continuous layer.

3. The surgical end effector according to claim 2, the conductive layer includes a first conductive trace and a second conductive trace, each of which is coupled to the strain gauge.

4. The surgical end effector according to claim 3, wherein the strain gauge includes a continuous trace having a first end and a second end, the first end coupled to the first conductive trace and the second end coupled to the second conductive trace.

5. The surgical end effector according to claim 4, wherein the strain gauge has a variable gauge factor.

6. The surgical end effector according to claim 5, wherein the strain gauge includes a pair of parallel grid lines, each of which has a tapered shape thereby providing the variable gauge factor.

7. The surgical end effector according to claim 6, wherein the strain gauge includes a plurality of grid lines of varying length providing the variable gauge factor.

8. The surgical end effector according to claim 1, further comprising:
   an anvil assembly; and
   a cartridge assembly including a plurality of fasteners.

9. The surgical end effector according to claim 8, wherein the drive assembly is configured to move at least one of the anvil assembly or the cartridge assembly relative to each other.

10. A surgical end effector comprising:
a housing;
a drive assembly movable within the housing; and
a strain gauge circuit disposed within the housing, the strain gauge circuit configured to measure a strain imparted on the housing by the drive assembly, the strain gauge circuit includes a strain gauge portion and a lead portion having a slack portion with at least one turn.

11. The surgical end effector according to claim 10, further comprising:
an anvil assembly; and
a cartridge assembly including a plurality of fasteners.

12. The surgical end effector according to claim 11, wherein the drive assembly is configured to move at least one of the anvil assembly or the cartridge assembly relative to each other.

13. A surgical instrument comprising:
a handle assembly including a controller and a power source;
a longitudinal shaft including a proximal end portion coupled to the handle assembly and a distal end portion; and
a surgical end effector having:
a housing;
a drive assembly movable within the housing; and
a strain gauge circuit disposed within the housing and electrically coupled to the controller and the power source, the strain gauge circuit configured to measure a strain imparted on the housing by the drive assembly and to transmit a measurement signal to the controller, the strain gauge circuit includes a flexible circuit, the flexible circuit having:
a first flexible dielectric substrate;
a resistive sensor layer disposed over the first flexible dielectric substrate;
a conductive layer disposed over the resistive sensor layer; and
a second flexible dielectric substrate disposed over the resistive sensor layer and the conductive layer.

14. The surgical instrument according to claim 13, wherein the resistive sensor layer includes a strain gauge and a continuous layer.

15. The surgical instrument according to claim 14, the conductive layer includes a first conductive trace and a second conductive trace, each of which is coupled to the strain gauge.

16. The surgical instrument according to claim 15, wherein the strain gauge includes a continuous trace having a first end and a second end, the first end coupled to the first conductive trace and the second end coupled to the second conductive trace.

17. The surgical instrument according to claim 16, wherein the strain gauge includes a variable cross-section.

18. The surgical instrument according to claim 17, wherein the strain gauge includes a pair of parallel grid lines, each of which has a tapered shape thereby providing the variable cross-section.

19. The surgical instrument according to claim 17, wherein the strain gauge includes a plurality of grid lines of varying length providing the variable cross-section.

* * * * *